United States Patent
Oh et al.

(10) Patent No.: US 10,044,449 B2
(45) Date of Patent: Aug. 7, 2018

(54) RECEPTION DEVICE AND TRANSMISSION/RECEPTION SYSTEM INCLUDING THE SAME

(71) Applicant: Electronics and Telecommunications Research Institute, Daejeon (KR)

(72) Inventors: Kwang Il Oh, Daejeon (KR); Tae Wook Kang, Daejeon (KR); Sung Eun Kim, Daejeon (KR); Hyung-Il Park, Daejeon (KR); Sung Weon Kang, Daejeon (KR); In Gi Lim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/590,652

(22) Filed: May 9, 2017

(65) Prior Publication Data
US 2018/0006734 A1  Jan. 4, 2018

(30) Foreign Application Priority Data

Jul. 4, 2016 (KR) .......... 10-2016-0084277
Nov. 18, 2016 (KR) .......... 10-2016-0154391

(51) Int. Cl.
*H04B 5/00* (2006.01)
*H04B 13/00* (2006.01)
(Continued)

(52) U.S. Cl.
CPC ........... *H04B 13/005* (2013.01); *B60R 25/24* (2013.01); *G06F 19/30* (2013.01); *H04B 5/0012* (2013.01); *H04B 5/0031* (2013.01); *H04B 5/0062* (2013.01); *H04B 7/0619* (2013.01)

(58) Field of Classification Search
CPC ....................................................... H04B 5/00
See application file for complete search history.

(56) References Cited

U.S. PATENT DOCUMENTS

| 6,944,496 B2 | 9/2005 | Jeong et al. |
| 8,625,557 B2 * | 1/2014 | Fukuda .................. G06F 1/163 370/338 |

(Continued)

FOREIGN PATENT DOCUMENTS

| JP | 3425347 B2 | 7/2003 |
| JP | 5033818 B2 | 9/2012 |

(Continued)

*Primary Examiner* — Cindy Trandai (57) ABSTRACT

The reception device includes a base member, a first electrode, a second electrode, a differential amplifier, and a circuit board. The base member includes a first surface and a second surface. The first electrode is provided on the first surface and configured to receive a reception signal. The second electrode is provided on the second surface and configured to receive a reference voltage. The differential amplifier is configured to amplify a potential difference between the reception signal and the reference voltage. The circuit board is configured to provide a power voltage and a reference ground to the differential amplifier. A distance between the circuit board and the first electrode is smaller than a distance between the circuit board and the second electrode. According to an embodiment of the inventive concept, the amplification performance of the reception device using a human body as a medium is improved.

18 Claims, 8 Drawing Sheets

(51) Int. Cl.
*G06F 19/00* (2018.01)
*H04B 7/06* (2006.01)
*B60R 25/24* (2013.01)

(56) References Cited

U.S. PATENT DOCUMENTS

| | | |
|---|---|---|
| 9,065,558 B2 | 6/2015 | Song et al. |
| 2002/0030585 A1* | 3/2002 | Doi ............ A61B 5/0028 340/5.64 |
| 2004/0092296 A1* | 5/2004 | Minotani ........ H04B 1/3827 455/575.6 |
| 2008/0045843 A1* | 2/2008 | Tsuji ............ A61B 5/0006 600/481 |
| 2008/0205904 A1* | 8/2008 | Shinagawa ........ G06F 1/163 398/186 |
| 2010/0141280 A1 | 6/2010 | Yang et al. |
| 2010/0219880 A1* | 9/2010 | Bae ............... H03K 5/082 327/513 |
| 2010/0307795 A1* | 12/2010 | Chen ............... H05K 1/025 174/250 |
| 2010/0308118 A1* | 12/2010 | Kataya ............. H01Q 7/00 235/492 |
| 2010/0315206 A1* | 12/2010 | Schenk ........... A61B 5/0024 340/286.01 |
| 2011/0139489 A1* | 6/2011 | Yoon ............. H05K 1/0227 174/250 |
| 2013/0113938 A1* | 5/2013 | Miyaki ............. H04N 5/30 348/163 |
| 2015/0271753 A1* | 9/2015 | Matsuda ......... H04W 52/0219 370/311 |
| 2016/0050516 A1* | 2/2016 | Visweswara ...... H04B 13/005 455/41.2 |
| 2016/0211744 A1* | 7/2016 | Arakawa ............ H02M 3/07 |
| 2017/0111123 A1* | 4/2017 | Ouzounov ....... H04B 13/005 |

FOREIGN PATENT DOCUMENTS

| | | |
|---|---|---|
| KR | 10-201-0045126 A | 5/2010 |
| KR | 10-2010-0120042 A | 11/2010 |

* cited by examiner

RECEPTION DEVICE AND TRANSMISSION/RECEPTION SYSTEM INCLUDING THE SAME

CROSS-REFERENCE TO RELATED APPLICATIONS

This U.S. non-provisional patent application claims priority under 35 U.S.C. § 119 of Korean Patent Application Nos. 10-2016-0084277, filed on Jul. 4, 2016, and 10-2016-0154391, filed on Nov. 18, 2016, the entire contents of which are hereby incorporated by reference.

BACKGROUND

The present disclosure herein relates to a reception device and a transmission/reception system including the same, and more particularly, to a reception device for performing communication by using a human body as a medium and a transmission/reception system including the same.

A signal transmission medium is needed to exchange signals between a transmission device and a reception device. Generally, there is a communication method using a wire, but such a communication method requires a cable between a transmission device and a reception device so that portability becomes an issue. Accordingly, various types of wireless communications have been developed for communication of portable terminals and the like.

In addition, communication methods for delivering signals or information from a transmission device to a reception device by using a human body as a medium have emerged in recent medium. Devices that exchange signals by using a human body as a medium may be applied to various fields such as medical, security, retail, and smart management. Since a communication method using a human body as a medium delivers signals by allowing the human body to contact a transmission/reception device, a separate wired signal transmission medium is not required and data may be transmitted and received between a user and a system. In addition, since a communication method using a human body as a medium does not transmit signals to the air as compared to a wireless communication, it has a binding force with respect to the signals.

There is a continuing need for a reception device and a transmission/reception system for ensuring the stability of such a reception device using a human body as a medium.

SUMMARY

The present disclosure provides a reception device for obtaining stability during signal amplification and a transmission/reception system including the same.

An embodiment of the inventive concept provides a reception device includes a base member, a first electrode, a second electrode, a differential amplifier, a circuit board, and a reception data processing unit.

The base member may include a first surface and a second surface for forming different outer surfaces. The first surface and the second surface may form different outer surfaces of the base member. The first surface and the second surface may be spaced from each other.

The first electrode may be provided on the first surface. The first electrode may receive a reception signal. The reception signal may be a digital signal. The first electrode may be configured to contact a human body.

The second electrode may be provided on the second surface. The second electrode may receive a reference voltage having a smaller voltage level than the reception signal. The second electrode may be spaced from a human body.

The differential amplifier may amplify a potential difference between the reception signal and the reference voltage to generate an amplification signal. A positive input terminal of the differential amplifier may receive the reception signal and a negative input terminal of the differential amplifier may receive the reference voltage. Alternatively, a negative input terminal of the differential amplifier may receive the reception signal and a positive input terminal of the differential amplifier may receive the reference voltage. The differential amplifier may have power noise reduction characteristics. The data processing unit may correct an amplification signal as restoration data.

The circuit board may provide a power voltage and a reference ground to the differential amplifier. A distance between the circuit board and the first electrode may be smaller than a distance between the circuit board and the second electrode. The circuit board may include a power plane and a ground plane. The power plane may provide a power voltage to the differential amplifier and the ground plane may provide a reference ground to the differential amplifier. A distance between the first electrode and the ground plane may be smaller than a distance between the first electrode and the second electrode. The circuit board may contact the first electrode. The circuit board may further include an insulating layer for electrically insulating the first electrode, the power plane, and the ground plane. A hole may be provided in the circuit board, and the first electrode and the differential amplifier may be electrically connected to each other through the hole.

The reception device may further include a display unit. The reception data processing unit may receive and correct an amplification signal. The display unit may receive an image signal from the reception data processing unit to display an image. In this case, the display unit may be provided on the third surface for forming an outer surface, which are different from the first surface and the second surface.

In an embodiment of the inventive concept, a transmission/reception system includes a transmission device and a reception device. The transmission device may include a signal generation unit, a transmission electrode, a transmission device ground, and a transmission data processing unit. The signal generation unit may generate a transmission signal and the transmission electrode may receive the transmission signal and provide it to a human body. The transmission device ground may provide a reference ground to the signal generation unit. The transmission data processing unit provides transmission signal information to the signal generation unit.

The reception device may include a base member, a first electrode, a second electrode, a differential amplifier, and a circuit board. A potential value of the reference ground of the reception device or a potential value of the transmission device ground may be different from a potential value of the ground surface. The first electrode and the transmission electrode may be configured to contact a human body. The second electrode may be configured to be spaced from a human body. The reception data processing unit generates restoration data having the same data as the transmission signal and a clock signal having the same clock as the transmission signal based on the amplification signal.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

In the following, embodiments of the inventive concept will be described in detail so that those skilled in the art easily carry out the present invention.

Figure 1:
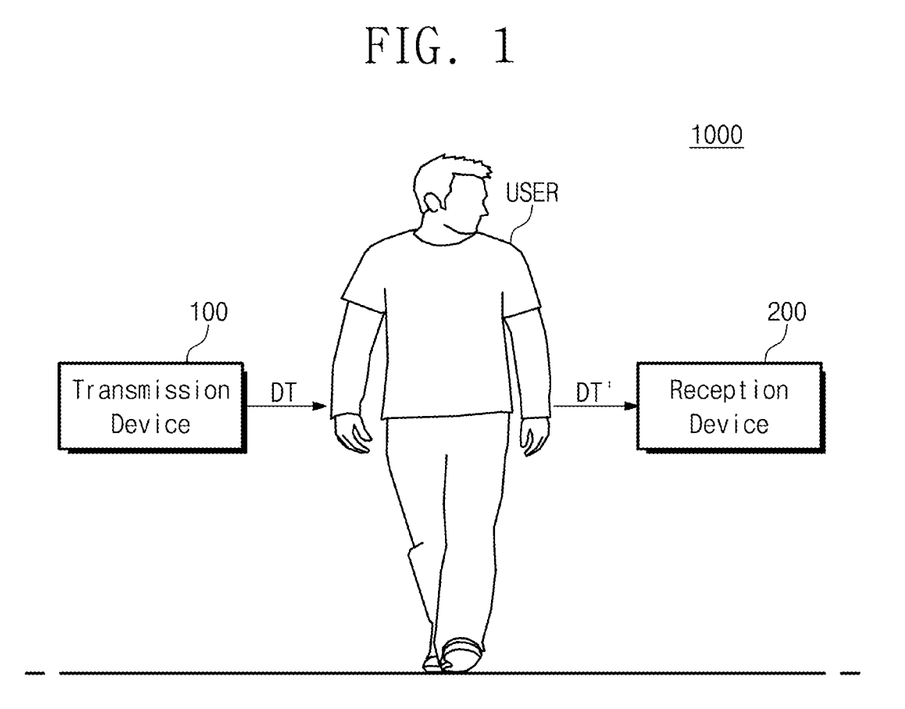
FIG. 1 is a view illustrating a transmission/reception system according to an embodiment of the inventive concept.

FIG. 1 is a view illustrating a transmission/reception system according to an embodiment of the inventive concept.

Referring to FIG. 1, a transmission/reception system 1000 includes a transmission device 100 and a reception device 200. The transmission/reception system 1000 transmits information from the transmission device 100 to the reception device 200 via a user USER. That is, the transmission/reception system 1000 exchanges signals and information by using a human body as a medium. However, the transmission medium of signals and information is not limited to a human body such as a user, but may be applied to living bodies such as animals and plants, and may use various other media. For convenience of description, it is assumed that the transmission medium of the transmission/reception system 1000 is the user USER, i.e., a human body.

The transmission device 100 generates a transmission signal DT. The transmission device 100 transmits the transmission signal DT to the user USER. The transmission device 100 may contact the user USER or transmit the transmission signal DT as spaced a small distance from the skin of a human body. The transmission device 100 may have a small size so that the user USER easily carries it. The transmission device 100 may be attached to the user USER to maintain a contact state with the user USER.

The user USER receives the transmission signal DT from the transmission device 100 and provides a reception signal DT' to the reception device 200. The transmission signal DT may be attenuated or delayed as the reception signal DT' by the resistance of the user USER itself, an electric field between the user USER and the transmission 100, and an electric field between the user USER and the reception device 200 Since the transmission signal DT is transmitted to the reception device 200 by using a human body as a medium, a binding force with respect to the signal is secured. Accordingly, the transmission device 100 may not deliver a signal to a human body by modulating a digital signal into an analog signal but may deliver a digital signal to a human body directly. That is, the transmission signal DT may be a digital signal. However, the inventive concept is not limited to this, and the transmission signal DT may be an analog signal.

The reception device 200 receives the reception signal DT' from the user USER. The reception device 200 may contact the user USER or receive the reception signal DT' as spaced a small distance from the skin of a human body. The reception device 200 may have a small size so that the user USER easily carries it. For example, the reception device 200 may include various portable devices such as a mobile terminal, a PDA, and a smart card. The reception device 200 may be attached to the user USER to maintain a contact state with the user USER. The reception device 200 may be a wearable device. For example, the reception device 200 may include various human contact devices such as smart watches, glasses, and necklaces.

Figure 2:
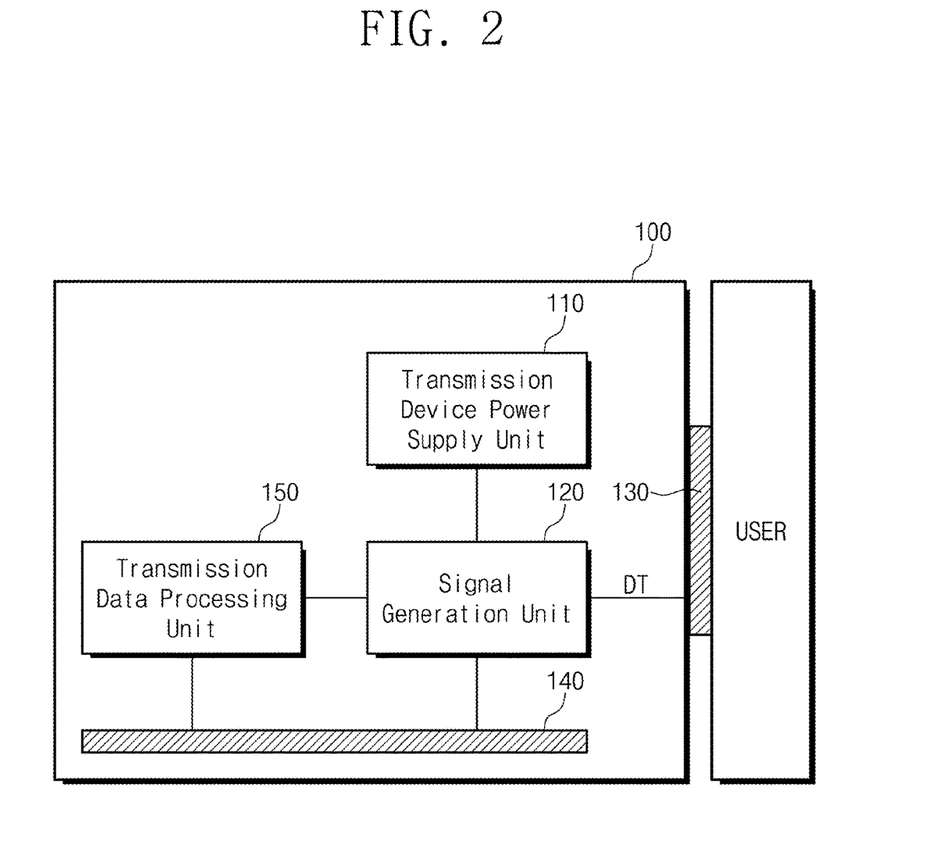
FIG. 2 is a block diagram illustrating a transmission device according to an embodiment of the inventive concept.

FIG. 2 is a block diagram illustrating a transmission device according to an embodiment of the inventive concept.

Referring to FIG. 2, a transmission device 100 includes a transmission device power supply unit 110, a signal generation unit 120, a transmission electrode 130, a transmission device ground 140, and a transmission data processing unit 150.

The transmission device power supply unit 110 provides power to the signal generation unit 120. A power voltage is provided to the signal generation unit 120 based on a potential difference formed between the transmission device power supply unit 110 and the transmission device ground 140.

The signal generation unit 120 generates a transmission signal DT based on the power voltage provided from the transmission device power supply unit 110. The signal generation unit 120 is electrically connected to the transmission device ground 140. The transmission signal DT is generated based on a potential difference formed between the signal generation unit 120 and the transmission device ground 140. The signal generation unit 120 may generate the transmission signal DT based on a signal received from the outside of the transmission device 100. In this case, the signal generation unit 120 may include a modulator for modulating an analog signal received from the outside. Alternatively, the signal generation unit 120 may generate the waveform of the transmission signal DT therein. The signal generation unit 120 may include an amplifier for amplifying the waveform of a signal to be provided to a user USER.

The transmission electrode 130 is electrically connected to the signal generation unit 120 and receives the transmission signal DT from the signal generation unit 120. The transmission electrode 130 may be formed on the outer surface of the transmission device 100 to deliver the transmission signal DT to the user USER. The transmission device 130 contacts the user USER or is spaced to have a small interval from the skin of a human body. Although not shown in the drawing, a protection layer for protecting the transmission electrode 130 may be disposed on the transmission electrode 130.

A capacitance is formed between the transmission electrode 130 and the user USER and a voltage induced at the transmission electrode 130 forms an electric field between the user USER and the transmission electrode 130 by the capacitance. Charges are induced at the skin of a human body by an electric field formed between the transmission device 130 and the user USER. In such a manner, the transmission electrode 130 provides the transmission signal DT to the user USER.

The transmission device ground 140 is formed inside the transmission device 100. The transmission device 100 may not be directly connected to the ground surface. Therefore, the potential of the transmission device ground 140 and the potential of the external ground of the transmission device 100 may be different. However, the transmission device ground 140 may form an electric field with the ground surface, and the transmission device ground 140 provides a reference ground to the transmission device 100. As a strong electric field is formed between the transmission device ground 140 and the ground surface, a potential difference between the ground of the ground surface and the transmission device ground 140 becomes smaller, so that the transmission performance of the transmission signal DT is improved. In order to form a strong electric field between the transmission device ground 140 and the ground surface, the transmission device ground 140 may be formed throughout the transmission device 100 to widen the area facing the ground surface. The transmission device ground 140 may be provided in the form of a printed circuit board.

An electric field may also be formed between the transmission device ground 140 and the user USER. When the transmission device 100 contacts the user USER, the transmission device ground 140 is disposed adjacent to the user USER and an electric field due to a capacitance between the transmission device ground 140 and the user USER is formed. Accordingly, a reference ground provided from the transmission device ground 140 may become unstable due to an electric field formed between the transmission device ground 140 and the user USER. A change in reference ground may affect the transmission stability of the transmission signal DT.

The transmission data processing unit 150 provides transmission signal information to the signal generation unit 120. The transmission data processing unit 150 controls the signal generation unit 120 to generate the transmission signal DT. The transmission signal information may include data and clock signals for generating the transmission signal DT.

Figure 3:
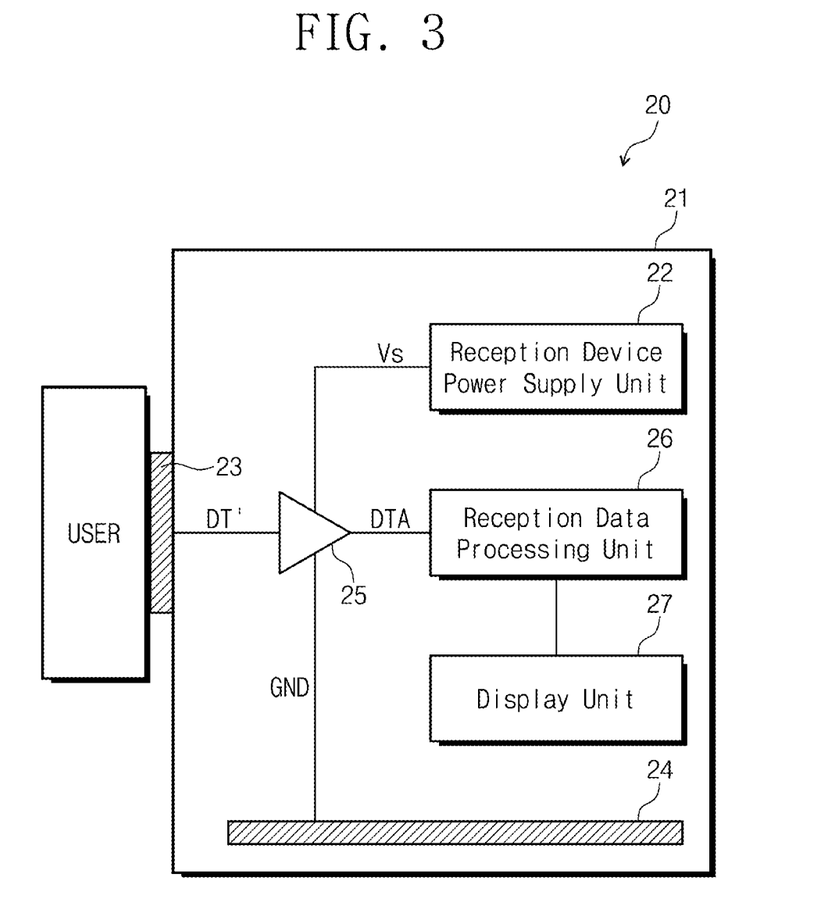
FIGS. 3 and 4 are views illustrating a reception device.
Figure 4:
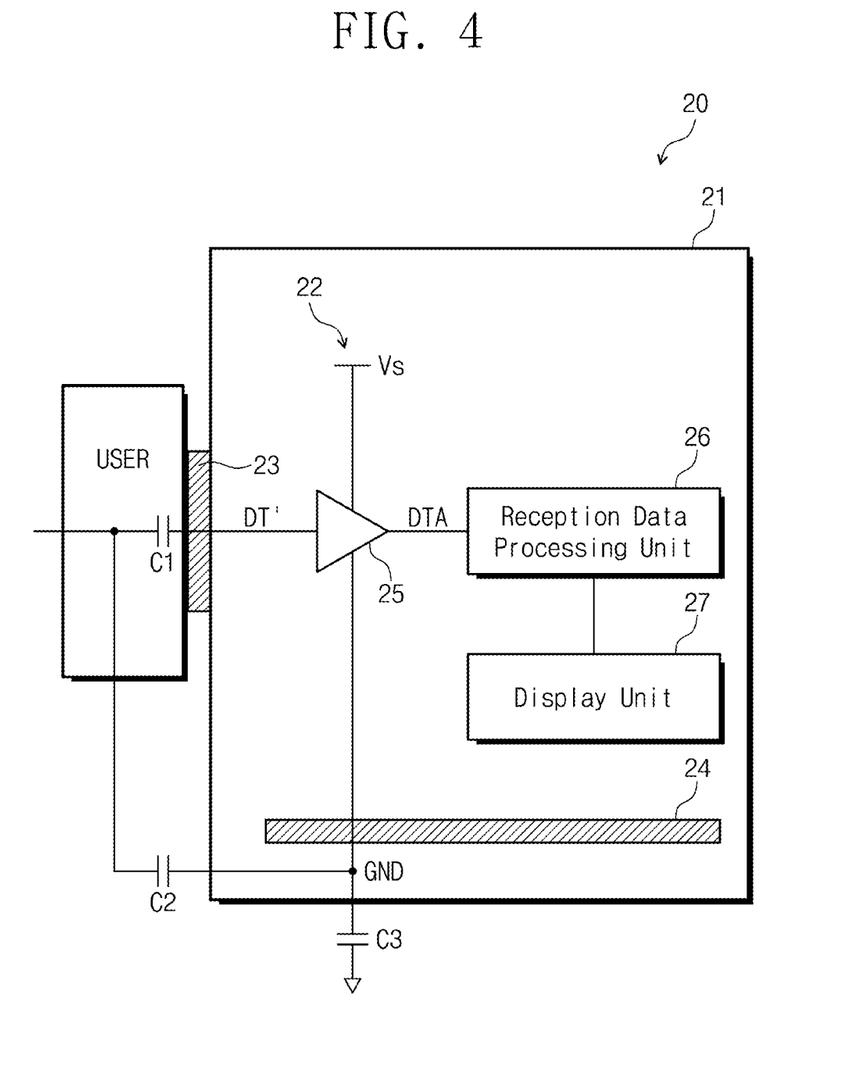

FIG. 3 is a block diagram illustrating a reception device of a transmission/reception system for transmitting a signal by using a human body as a medium. FIG. 4 is an equivalent circuit diagram of a reception device of FIG. 3.

Referring to FIG. 3, a reception device 20 includes a base member 21, a reception device power supply unit 22, a first electrode 23, a reception device ground 24, an amplifier 25, a reception data processing unit 26, and a display unit 27.

The base member 21 may accommodate the reception device power supply unit 22, the reception device ground 24, the amplifier 25, the reception data processing unit 26, and the display unit 27. The base member 21 may be formed to allow the user USER to carry or attach the reception device 20 easily.

The reception device power supply unit 22 is electrically connected to the amplifier 25. The reception device power supply unit 22 provides a power voltage Vs to the amplifier 25. The amplifier 25 receives the power voltage Vs based on a potential difference between the reception device power supply unit 22 and the reception device ground 24.

The first electrode 23 is provided at the external surface of the base member 21. The first electrode 23 may contact the user USER or may be spaced to have a small interval from the skin of a human body. The first electrode 23 receives a reception signal DT' from the user USER.

The reception device ground 24 is formed inside the reception device 20. The reception device ground 24 is formed throughout the reception device 20. The reception device ground 24 may be provided in the form of a printed circuit board. The reception device ground 24 provides a reference ground GND to the amplifier 25. The reception device 20 may not be directly connected to the ground surface. Therefore, the potential of the reception device ground 24 and the potential of the external ground of the reception device 20 may be different.

The amplifier 25 is electrically connected to the first electrode 23. The amplifier 25 receives the reception signal DT' from the first electrode 23. The amplifier 25 amplifies the reception signal DT' to generate an amplification signal DTA.

The reception data processing unit 26 may perform correction such as removing the noise by receiving the amplification signal DTA from the amplifier 25. The reception data processing unit 26 may restore the amplification signal DTA to the transmission signal DT. The reception data processing unit 26 may store the restored amplification signal DTA and may provide an image signal based on the restored amplification signal DTA to the display unit 27. The display unit 27 may receive an image signal from the reception data processing unit 26 and display an image.

Referring to FIG. 4, an electrical influence occurring during the process of receiving the reception signal DT' by the reception device 20 is shown in an equivalent circuit diagram. The reception device 20 forms a first capacitance C1, a second capacitance C2, and a third capacitance C3 due to an electrical influence with the user USER or the ground surface.

Although the first capacitance C1 in the user USER is shown in FIG. 4 to allow the first capacitance C1 to be clearly seen, it may be formed between the first electrode 23 and the user USER. The voltage induced in the user USER by the transmission signal DT provided by the transmission device 100 forms an electric field between the user USER and the first electrode 23 by the first capacitance C1. Charges are induced at the first electrode 23 by an electric field formed between the first electrode 23 and the user USER. In such a manner, the first electrode 23 receives the reception signal DT' from the user USER.

The second capacitance C2 is formed between the reception device ground 24 and the user USER. The reception device 20 is disposed close to a human body, and the reception device ground 24 is disposed adjacent to the user USER. Accordingly, the second capacitance C2 is formed between the reception device ground 24 and the user USER and an electric field is formed between the reception device ground 24 and the user USER.

The third capacitance C3 is formed between the reception device ground 24 and the ground surface. As the third capacitance C3 is formed, the reception device ground 24 provides the reference ground GND. As a strong electric field is formed between the reception device ground 24 and the ground surface, the stability of the reference ground GND is enhanced. In this case, the reception device 20 has improved reception performance of the reception signal DT'. That is, in the transmission/reception system including the reception device 20 of FIGS. 3 and 4, if the reference grounds GNDs of a transmission device and the reception device 20 are the same, signal transmission/reception performance is improved.

The input voltage of the amplifier 25 is defined with a relative size of a voltage induced at the first electrode 23 with respect to the reference ground of the reception device ground 24. It is difficult to continuously maintain the third capacitance C3 at a capacitance equal to or higher than a predetermined value in order to ensure the miniaturization and portability of the reception device 20. Since the reception device ground 24 is disposed adjacent to a human body due to the characteristics of the reception device 20 using the human body as a medium, when an interference signal identical to the reception signal DT' is provided to the reception device ground 24 through the second capacitance C2, the amplification performance of the reception signal DT' by the amplifier 25 is lowered. In addition, since the reception device 20 should provide a signal in a harmless range to a human body, it is difficult to overcome the amplification performance by increasing the size of a signal transmitted from the transmission device 100 to the reception device 20.

Figure 5:
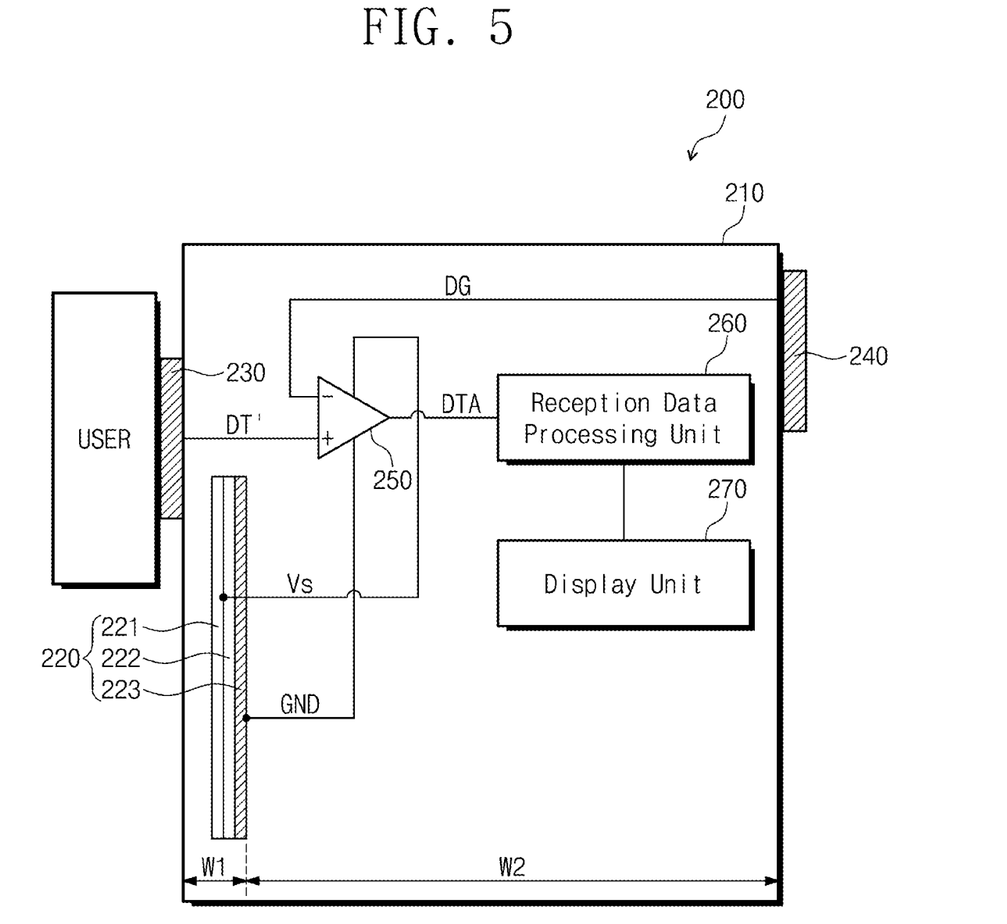
FIG. 5 is a block diagram illustrating a reception device according to an embodiment of the inventive concept.
Figure 6:
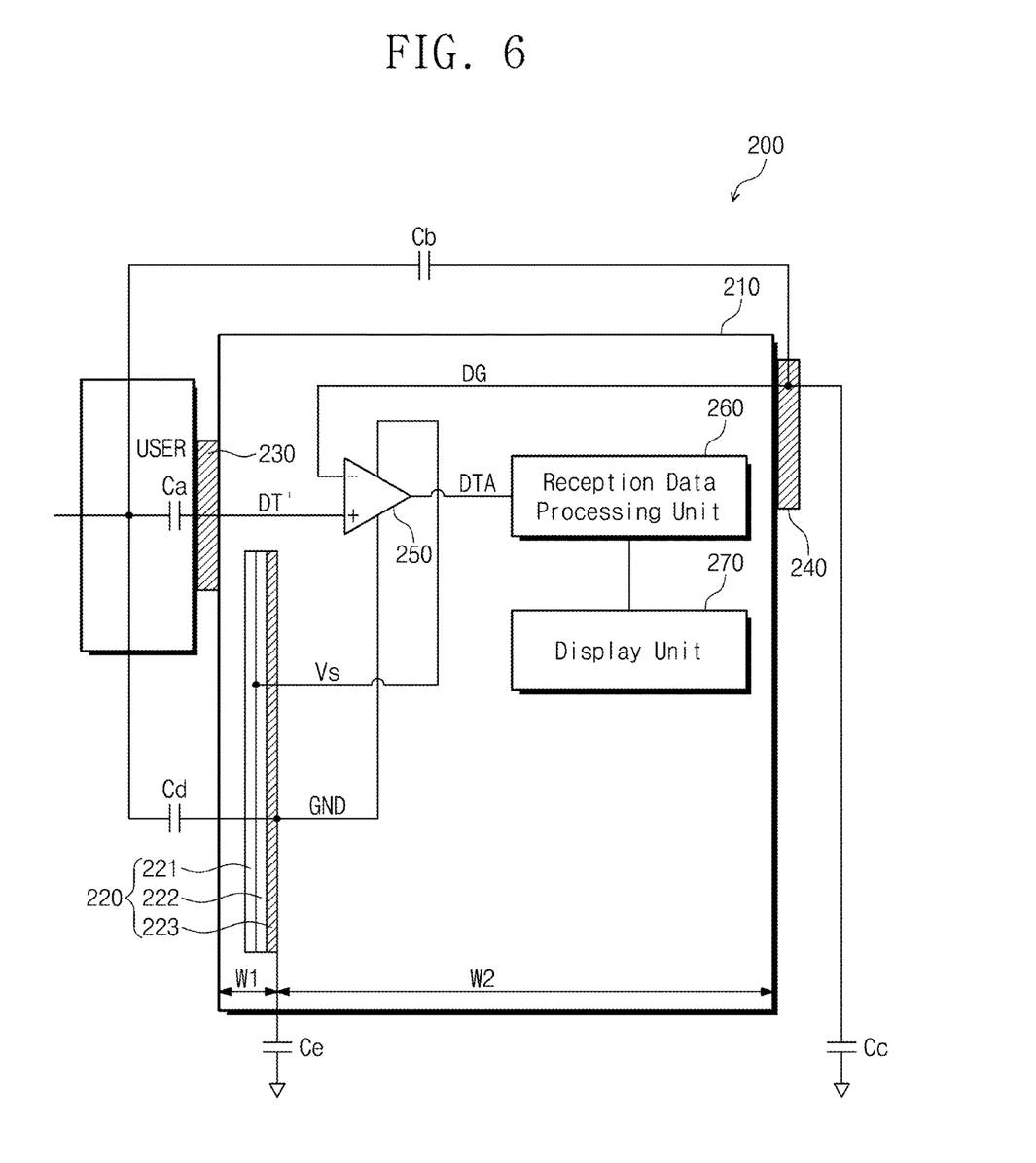
FIG. 6 is an equivalent circuit diagram of a reception device according to an embodiment of the inventive concept.

FIG. 5 is a block diagram illustrating a reception device according to an embodiment of the inventive concept. FIG. 6 is an equivalent circuit diagram of a reception device of FIG. 5.

Referring to FIG. 5, a reception device 200 includes a base member 210, a circuit board 220, a first electrode 230, a second electrode 240, a differential amplifier 250, a reception data processing unit 260, and a display unit 270.

The base member 210 may accommodate the circuit board 220, the differential amplifier 250, the reception data processing unit 260, and the display unit 270. The base member 210 may protect the circuit board 220, the differential amplifier 250, the reception data processing unit 260, and the display unit 270 from an external environment. The base member 210 may include an outer surface contacting a user USER.

The circuit board 220 includes a power plane 221, an insulating layer 222, and a ground plane 223. The insulating layer 222 is disposed between the power plane 221 and the ground plane 223 to electrically isolate the power plane 221 from the ground plane 223. Although it is shown in FIG. 5 that the power plane 221 is disposed further from the first electrode 230 than the ground plane 223, the inventive concept is not limited thereto and the power plane 221 may be disposed closer to the first electrode 230 than the ground plane 223. In addition, the circuit board 220 may further include an insulating layer (not shown) disposed to face the insulating layer 222 with the power plane 221 therebetween, and may further include an insulating layer (not shown) disposed to face the insulating layer 222 with the ground plane 223 therebetween.

The power plane 221 and the ground plane 223 are electrically connected to the differential amplifier 250. The power plane 221 provides a power voltage Vs to the differential amplifier 250. Although not shown in the drawing, the power plane 221 may be electrically connected to a power voltage supply unit for generating the power voltage Vs. The ground plane 223 provides a reference ground GND to the differential amplifier 250. Also, the ground plane 223 may perform a function for discharging charges formed on the circuit board 220. The differential amplifier 250 receives the power voltage Vs based on the potential difference between the power plane 221 and the ground plane 223. The ground plane 223 is spaced apart from the first electrode 230 to have a first width W1. The ground plane 223 is spaced apart from the second electrode 240 to have a second width W2. The first width W1 may be smaller than the second width W2. That is, the circuit board 220 may be disposed close to the user USER. This may be for disposing a circuit board for driving the display unit 270 between the circuit board 220 and the second electrode 240. In this case, a signal identical to the reception signal DT' may be provided to the ground plane 223 by an electrical influence between the circuit board 220 and the user USER. The second electrode 240, which will be described later, is implemented to secure amplification performance in the environment of the reception device 200.

The first electrode 230 is provided at the external surface of the base member 210. The first electrode 230 may contact the user USER or may be spaced to have a small interval from the skin of a human body. The first electrode 230 receives a reception signal DT' from the user USER.

The second electrode 240 is provided at the external surface of the base member 210. The second electrode 230 is provided at an external surface different from an external surface where the first electrode 230 is provided in order not to contact the user USER. The second electrode 240 receives a reference voltage DG based on an electric field with the user USER. The second electrode 240 is formed spaced apart from the first electrode 230 so as to minimize the formation of an electric field with the user USER or the first electrode 230. For example, the second electrode 240 may be provided at the opposite surface of the first electrode 230 so as to face the outer surface of the base member 210 where the first electrode 230 is provided.

The differential amplifier 250 is electrically connected to the first electrode 230 and the second electrode 240. The first electrode 230 may be electrically connected to the positive input terminal of the differential amplifier 250 and the second electrode 240 may be electrically connected to the negative input terminal of the differential amplifier 250. Alternatively, the first electrode 230 may be electrically connected to the negative input terminal of the differential amplifier 250, and the second electrode 240 may be electrically connected to the positive input terminal of the differential amplifier 250. The differential amplifier 250 amplifies and outputs a potential difference between the positive input terminal and the negative input terminal. The differential amplifier 250 amplifies a difference between the voltage level of the first electrode 230 and the voltage level of the second electrode 240 or amplifies a difference between the voltage level of the second electrode 240 and the voltage level of the first electrode 230, in order to generate an amplification signal DTA. That is, the differential amplifier 250 amplifies a potential difference between the reception signal DT' and the reference voltage DG (or a potential difference between the reference voltage DG and the reception signal DT') to generate the amplification signal DTA. Therefore, the differential amplifier 250 may amplify a signal by minimizing the influence of the reference ground GND provided by the ground plane 223. The amplification signal DTA may output a potential difference between the reception signal DT' and the reference voltage DG to the single output terminal of the differential amplifier 250 according to a set voltage gain. However, the inventive concept is not limited thereto, and the differential amplifier 250 may include a differential output based on a reference output voltage.

The differential amplifier 250 receives the power voltage Vs from the power plane 221. The differential amplifier 250 generates the amplification signal DTA based on the reception signal DT', the reference voltage DG, and the power voltage Vs. The differential amplifier 250 may include a power noise reduction circuit having a high power noise reduction ratio (PSRR).

The reception data processing unit 260 receives the amplification signal DTA from the differential amplifier 250. Although not shown in the drawing, the reception data processing unit 260 may include a band pass filter, a comparator, and a clock data restoration circuit. The band pass filter may remove the noise of the amplification signal DTA. The comparator and the clock data restoration circuit correct the amplification signal DTA to be restored to the same data and clock as the transmission signal DT provided by the transmission device 100. The reception data processing unit 260 generates restoration data having data corresponding to the transmission signal DT and a clock signal having the same clock as the transmission signal DT based on the amplification signal DTA. The reception data processing unit 260 may further include a storage for storing the amplification signal DTA, the restoration data, or the clock signal. Such a storage may include at least one of nonvolatile memory devices such as Read Only Memory (ROM), Programmable ROM (PROM), Electrically Programmable ROM (EPROM), Electrically Erasable and Programmable ROM (EEPROM), a flash memory device, Phase-change RAM (PRAM), Magnetic RAM (MRAM), Resistive RAM (RRAM), or Ferroelectric RAM (FRAM) or may include at least one of volatile memory devices such as Static RAM (SRAM), Dynamic RAM (DRAM) or Synchronous DRAM (SDRAM).

The display unit 270 may receive an image signal based on the restored amplification signal DTA from the reception data processing unit 260 and display an image. The display unit 270 may include at least one of a Liquid Crystal Display (LCD), an Organic Light Emitting Diode (OLED), an Active Matrix OGLED (AMOLED), a flexible display, or an electronic ink.

Referring to FIG. 6, an electrical influence occurring during the process of receiving the reception signal DT' by the reception device 200 is shown in an equivalent circuit diagram. The reception device 200 forms a first capacitance Ca, a second capacitance Cb, a third capacitance Cc, a fourth capacitance Cd, and a fifth capacitance Ce due to an electrical influence with the user USER or the ground surface.

Although the first capacitance Ca in the user USER is shown in FIG. 6 to allow the first capacitance Ca to be clearly seen, it may be formed between the first electrode 230 and the user USER. The fourth capacitance Cd is formed between the ground plane 223 and the user USER. The fifth capacitance Ce is formed between the ground plane 223 and the ground surface. The first capacitance Ca may correspond to the first capacitance C1 of FIG. 4, the fourth capacitance Cd may correspond to the second capacitance C2 of FIG. 4, and the fifth capacitance Ce may correspond to the third capacitance C3 of FIG. 4.

The second capacitance Cb is formed between the user USER and the second electrode 240. An electric field is formed between the user USER and the second electrode 240 and charges are induced at the second electrode 240. A distance between the user USER and the second electrode 240 is disposed to be longer than a distance between the user USER and the first electrode 230 or between the user USER and the ground plane 223. Accordingly, the size of an electric field formed between the user USER and the second electrode 240 is relatively small, and the reference voltage DG provided through the second capacitance Cb has a smaller than the reception signal DT' delivered through the first capacitance Ca or a signal transmitted to the ground plane 223 through the fourth capacitance Cd. Since the amplification signal DTA is generated based on a potential difference between the reception signal DT' and the reference voltage DG, as the size of an electric field formed between the second electrode 240 and the ground surface is smaller, the quality of the amplification signal DTA is improved.

The third capacitance Cc is formed between the second electrode 240 and the ground surface. An electric field between the second electrode 240 and the ground surface forms part of the reference voltage DG provided from the second electrode 240 to the differential amplifier 250. Since the amplification signal DTA is generated based on a potential difference between the reception signal DT' and the reference voltage DG, as a strong electric field is formed between the second electrode 240 and the ground surface, the stability of the amplification signal DTA is improved.

The differential amplifier 250 receives the reference voltage DG from the second electrode 240 and the reference voltage DG is generated by an electrical influence between the second electrode 240 and the user USER based on the second capacitance Cb and an electrical influence between the second electrode 240 and the ground surface based on the third capacitance Cc. Compared to the reception device 20 of FIGS. 3 and 4, the amplification signal DTA in the reception device 200 according to an embodiment of the inventive concept depends on a potential difference between the reception signal DT' and the reference voltage DG. That is, unlike the amplification signal DTA of FIG. 4 depending on a potential difference between the first electrode 23 and the reception device ground 24, the amplification signal DTA according to an embodiment of the inventive concept is hardly affected by an electric field between the ground plane 223 and the user USER. The differential amplifier 250 may include a circuit having a high PSRR. The differential amplifier 250 is connected to the power plane 221 to minimize the influence of an electric field between the ground plane 223 and the user USER. Even if a signal identical to the reception signal DT' provided to the first electrode 230 is provided to the ground plane 223, it may be reduced by a power noise reduction circuit. A distance between the circuit board 220 and the first electrode 230 has a first width W1 that is smaller than a second width W2 so that even if there is a great electrical influence between the user USER and the ground plane 223, the reference ground GND provided by the ground plane 223 hardly affects the stability of the amplification signal DTA. Therefore, it is regardless that the circuit board 220 is disposed close to the first electrode 230, and a value of the reference ground of the transmission device 100 and a value of the reference ground GND of the reception device 200 are not adjusted to be equal to each other.

Figure 7:
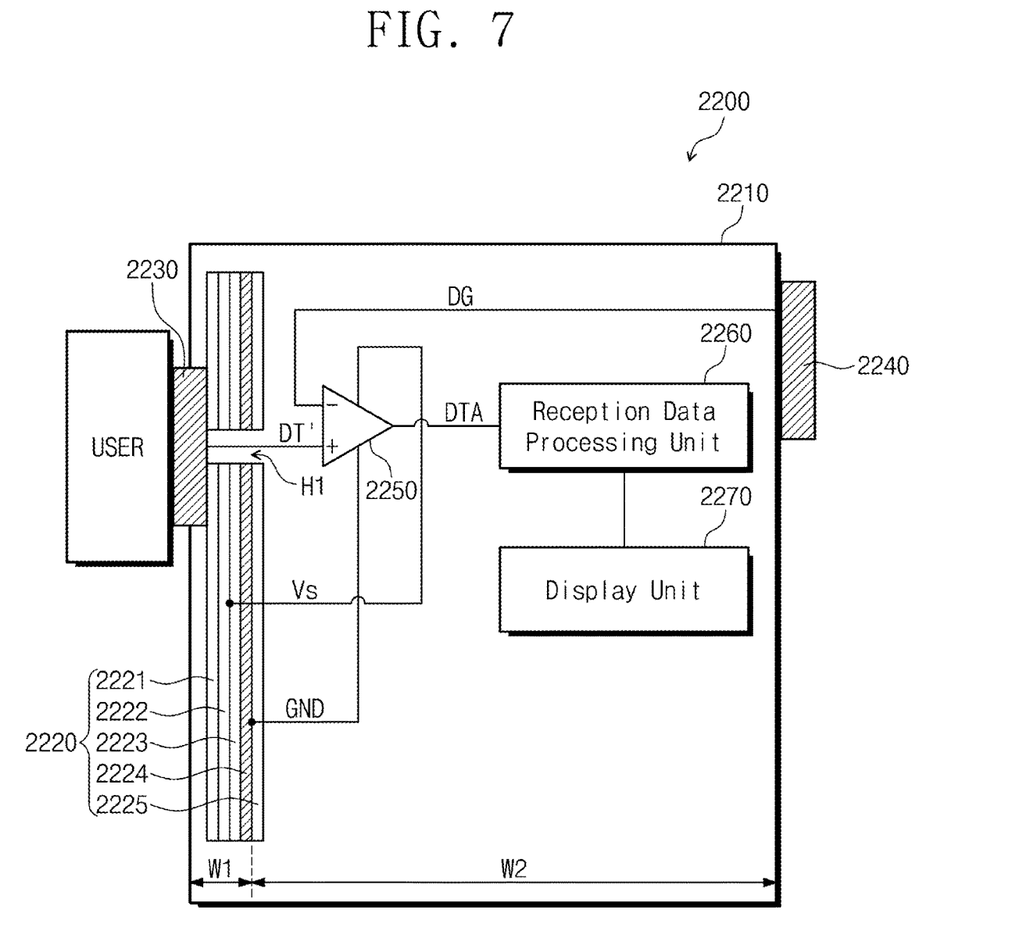
FIG. 7 is a block diagram illustrating a reception device according to another embodiment of the inventive concept.

FIG. 7 is a block diagram illustrating a reception device according to an embodiment of the inventive concept.

Referring to FIG. 7, a reception device 2200 includes a base member 2210, a circuit board 2220, a first electrode 2230, a second electrode 2240, a differential amplifier 2250, a reception data processing unit 2260, and a display unit 2270. The base member 2210, the first electrode 2230, the second electrode 2240, the differential amplifier 2250, the reception data processing unit 2260, and the display unit 2270 may have the same configuration as the base member 210, the first electrode 230, the second electrode 240, the differential amplifier 250, the reception data processing unit 260, and the display unit 270 of FIG. 5, and perform the substantially same functions, so that their detailed descriptions are omitted.

The circuit board 2220 includes a first insulating layer 2221, a power plane 2222, a second insulating layer 2223, a ground plane 2224, and a third insulating layer 2225. However, the circuit board 2220 is not limited thereto, and may have various layered structures and may include additional components. The circuit board 2220 may contact the first electrode 2230.

The first insulating layer 2221 contacts the first electrode 2230 and is disposed between the power plane 2222 and the first electrode 2230 to electrically insulate the power plane 2222 from the first electrode 2230. The power plane 2222 is electrically connected to and provides a power voltage Vs to the differential amplifier 2250. The second insulating layer 2223 is disposed between the power plane 2222 and the ground plane 2224 to electrically isolate the power plane 2222 from the ground plane 2224. The ground plane 2224 is electrically connected to and provides a reference ground GND to the differential amplifier 2250. The third insulating layer 2225 is disposed on the ground plane 2224 and prevents a short circuit between the ground plane 2224 and the differential amplifier 2250.

A distance between the circuit board 2220 and the first electrode 2230 may be disposed to be closer than a distance between the circuit board 2220 and the second electrode 2240. A circuit board for driving the display unit 2270 may be disposed between the circuit board 2220 and the second electrode 2240. As in FIG. 5, the reception device 2000 forms the second electrode 2240 so as to secure the amplification performance of the reception signal DT' without depending on the electrical influence between the circuit board 2220 and the user USER.

The circuit board 2220 may form a hole H1 to secure a wiring path for electrically connecting the first electrode 2230 to the positive input terminal (or negative input terminal) of the differential amplifier 2250. The shape of the hole H1 may be cylindrical, but is not limited thereto and may have various shapes. An insulating film may be provided in the hole H1 so that the power plane 2222 or the ground plane 2224 is not electrically connected to the first electrode 2230.

Figure 8:
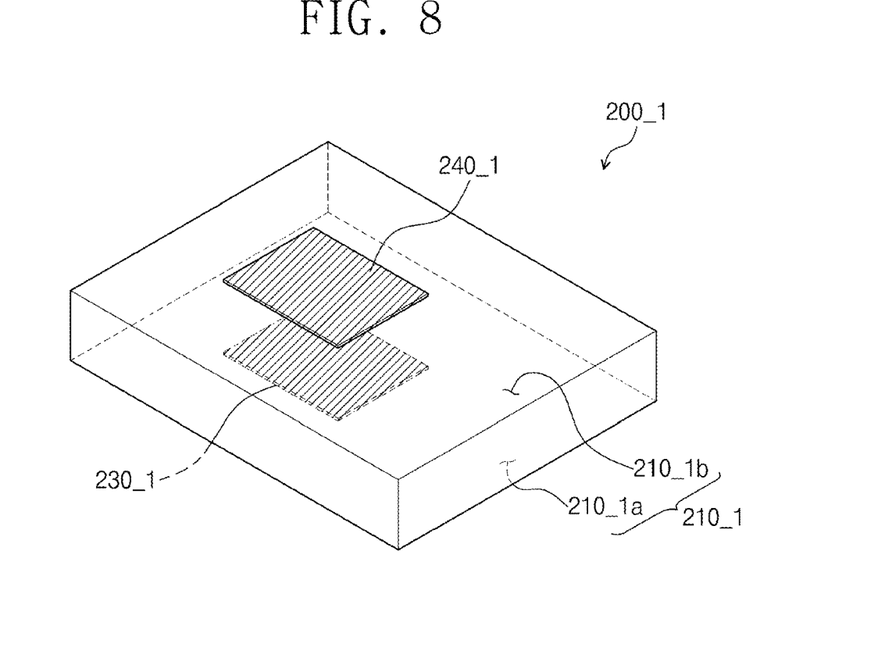
FIGS. 8 and 9 are perspective views of a reception device according to an embodiment of the inventive concept.
Figure 9:
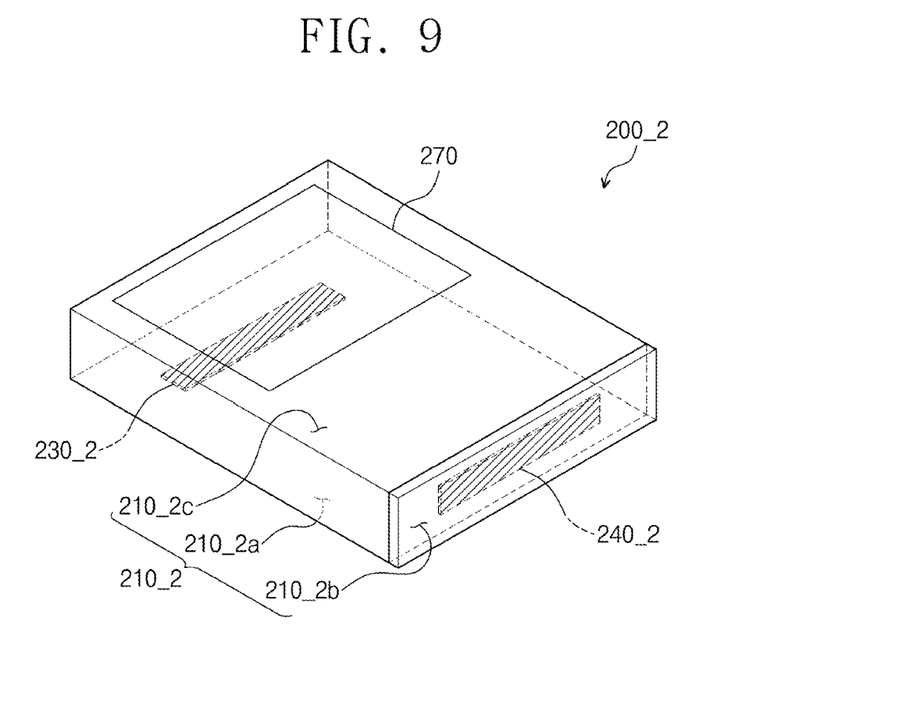

FIGS. 8 and 9 are perspective views of reception devices 200_1 and 200_2 according to an embodiment of the inventive concept.

Referring to the reception device 200_1 of FIG. 8, the base member 210_1 includes a first surface 210_1a and a second surface 210_1b. The first surface 210_1a and the second surface 210_1b are disposed to face each other. The first surface 210_1a and the second surface 210_1b are spaced apart from each other not to contact each other. The first surface 210_1a and the second surface 210_1b may be disposed in parallel, but are not limited thereto.

The first electrode 230_1 is provided on the first surface 210_1a. The first electrode 230_1 may be disposed on the first surface 210_1a so as to be exposed to the outside. Alternatively, the first electrode 230_1 may be disposed inside the first surface 210_1a so as not to be directly exposed to the outside. In this case, the first surface 210_1a of the base member 210_1 may have a thin thickness to facilitate receiving signals from a human body. The first surface 210_1a may be configured to contact the user USER or to be spaced at a fine interval so that the first electrode 230_1 receives the reception signal DT'. The first surface 210_1a is disposed closer to the user USER than the second surface 210_1b. It may be fixed to maintain the contact state of the first surface 210_1a and the user USER in order to improve the reception stability of the reception device 200_1. For example, the reception device 200_1 may be formed so that the first surface 210_1a is detachable from the user USER. Although not shown in the drawing, the reception device 200_1 may further include a thin protective layer to prevent the first electrode 230_1 or the first surface 210_1a contacting a human body from being damaged from the human body.

The second electrode 240_1 is provided on the second surface 210_1b. The second electrode 240_1 may be disposed on the second surface 210_1b so as to be exposed to the outside. Alternatively, the second electrode 240_1 may be disposed inside the second surface 210_1b so as not to be directly exposed to the outside. The second surface 210_1b may be configured to be spaced apart from the user USER so that an electrical influence between the second electrode 240_1 and the user USER is minimized. The second surface 210_1b is configured to be disposed farther away from the user USER than the first surface 210_1a. For example, the second surface 210_1b may be the opposite surface of the first surface 210_1a. However, the inventive concept is not limited thereto, and the second surface 210_1b may be formed at various positions so as to secure a separation distance from the user USER or the first electrode 230_1. Although not shown in the drawing, the reception device 200_1 may further include a protective layer to protect the second electrode 240_1 from an external environment or prevent the second electrode 240_1 from contacting the user USER directly.

As described above, the first surface 210_1a contacts the user USER, and the second surface 210_1b is spaced apart from the user USER. However, on the contrary, the second surface 210_1b may contact the user USER, and the first surface 210_1a may be spaced apart from the user USER. In this case, the reception device 200_1 of the inventive concept may receive the reception signal DT' through the second electrode 240_1 and receive the reference voltage DG through the first electrode 230_1. Referring to FIGS. 5 and 6, since the differential amplifier 250 amplifies a potential difference between the positive input terminal and the negative input terminal, when the second surface 210_1b contacts the user USER, only the polarity of an amplification signal is changed and the characteristics of the remaining amplification signal are the same, as compared with the case that the first surface 210_1a contacts the user USER. Accordingly, the reception device 200_1 may be configured so that one of the first surface 210_1a or the second surface 210_1b contacts the user USER.

Referring to the reception device 200_2 of FIG. 9, the base member 210_2 includes a first surface 210_2a, a second surface 210_2b, and a third surface 210_2c. The first surface 210_2a and the second surface 210_2b are disposed to face different directions. The first surface 210_2a and the second surface 210_2b may have an intersection line. The first surface 210_2a and the second surface 210_2b may be disposed vertically, but are not limited thereto. The first surface 210_2a and the third surface 210_2c are disposed to face each other. The first surface 210_2a and the third surface 210_2c are spaced apart from each other not to contact each other. The first surface 210_2a and the third surface 210_2c may be disposed in parallel, but are not limited thereto.

The first electrode 230_2 is provided on the first surface 210_2a. Since there is something in common that the first electrode 230_1 and the first surface 210_1a of FIG. 7 and the first electrode 230_2 and the first surface 210_2a of FIG. 8 are configured to contact or to be spaced a fine interval away from the user USER, detailed descriptions are omitted.

The second electrode 240_2 is provided on the second surface 210_2b. The second surface 210_2b may be configured to minimize an electrical influence between the second electrode 240_2 and the user USER. For example, the second electrode 240_2 may be formed to overlap the intersection line of the second surface 210_2b and the third surface 210_2c in order to secure a separation distance from the user USER. However, the inventive concept is not limited thereto, and the second electrode 240_2 may be formed at various positions so as to secure a separation distance from the user USER or the first electrode 230_2. The reception device 200_2 may further include the protective layer 290 to protect the second electrode 240_2 from an external environment or prevent the second electrode 240_2 from contacting the user USER directly.

The display unit 270 may be provided on the third surface 210_2c in order to display an image. That is, the third surface 210_2c may provide the user USER with visual feedback about the information on the reception signal DT'. In addition, the third surface 210_2c may provide components for providing various sensory feedbacks. The second electrode 240_2 may be disposed on one side surface of the reception device 200_2 including the second surface 210_2b to ensure the availability of the third surface 210_2c.

A reception device and a transmission/reception system including the same according to an embodiment of the inventive concept may improve the amplification performance of a reception signal.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A reception device for human body communication, the reception device comprising:
    a base member including a first outer surface and a second outer surface;
    a first electrode provided on the first outer surface and configured to receive a reception signal;
    a second electrode provided on the second outer surface and configured to receive a reference voltage having a smaller voltage level than the reception signal;
    a differential amplifier configured to amplify a potential difference between the reception signal and the reference voltage to generate an amplification signal;
    a circuit board comprising a power plane configured to provide a power voltage to the differential amplifier, a ground plane configured to provide a reference ground to the differential amplifier, and an insulation plane separating the ground plane from the power plane; and
    a reception data processing unit configured to correct the amplification signal as restoration data,
    wherein a distance between the ground plane and the first electrode is smaller than a distance between the ground plane and the second electrode.

2. The reception device of claim 1, wherein the first electrode is configured to contact a human body and the second electrode is configured to be spaced from the human body.

3. The reception device of claim 1, wherein the first surface and the second surface are spaced apart from each other.

4. The reception device of claim 1, wherein a distance between the first electrode and the ground plane is smaller than a distance between the first electrode and the second electrode.

5. The reception device of claim 1, wherein the circuit board contacts the first electrode.

6. The reception device of claim 5, wherein the circuit board further comprises an insulating layer for electrically insulating the first electrode, the power plane, and the ground plane.

7. The reception device of claim 6, wherein a hole is provided in the circuit board, and the first electrode and the differential amplifier are electrically connected to each other through the hole.

8. The reception device of claim 1, wherein a positive input terminal of the differential amplifier receives the reception signal and a negative input terminal of the differential amplifier receives the reference voltage.

9. The reception device of claim 1, wherein a negative input terminal of the differential amplifier receives the reception signal and a positive input terminal of the differential amplifier receives the reference voltage.

10. The reception device of claim 1, further comprising a display unit configured to receive an image signal based on the amplification signal from the reception data processing unit and display an image.

11. The reception device of claim 10, wherein the base member further comprises a third outer surface facing the first outer surface and the display unit is provided on the third outer surface.

12. The reception device of claim 1, wherein the reception signal is a digital signal.

13. The reception device of claim 1, further comprising a protective layer configured to cover the first electrode or the second electrode.

14. A transmission/reception system for human body communication, the transmission/reception system comprising:
    a transmission device configured to provide a transmission signal; and
    a reception device configured to receive a reception signal based on the transmission signal,
    wherein the reception device comprises:
    a base member including a first outer surface and a second outer surface for forming different outer surfaces;
    a first electrode provided on the first outer surface and configured to receive the reception signal;
    a second electrode disposed on the second outer surface and configured to receive a reference voltage having a smaller voltage level than the reception signal;
    a differential amplifier configured to amplify a potential difference between the reception signal and the reference voltage;
    a circuit board comprising a power plane configured to provide a power voltage to the differential amplifier, a ground plane configured to provide a reference ground to the differential amplifier, and an insulation plane separating the ground plane form the power plane; and
    a reception data processing unit configured to correct the amplification signal as restoration data,
    wherein a distance between the ground plane and the first electrode is smaller than a distance between the ground plane and the second electrode.

15. The transmission/reception system of claim 14, wherein the reception data processing unit generates restoration data having the same data as the transmission signal and a clock signal having the same clock as the transmission signal based on the amplification signal.

16. The transmission/reception system of claim 14, wherein the transmission device comprises:
    a signal generation unit configured to generate the transmission signal;
    a transmission data processing unit configured to provide transmission signal information to the signal generation unit;

a transmission electrode configured to receive the transmission signal from the signal generation unit to provide the received transmission signal to the reception device; and a transmission device ground configured to provide a reference ground to the signal generation unit.

17. The transmission/reception system of claim 16, wherein a potential value of the reference ground of the reception device or a potential value of the transmission device ground is different from a potential value of a ground surface.

18. The transmission/reception system of claim 16, wherein the first electrode and the transmission electrode are configured to contact a human body and the second electrode is configured to be spaced from the human body.

* * * * *